(12) United States Patent
Kuroda et al.

(10) Patent No.: US 8,781,569 B2
(45) Date of Patent: Jul. 15, 2014

(54) BIOMETRIC INFORMATION PROCESSING DEVICE, BIOMETRIC INFORMATION PROCESSING METHOD, AND CONTROL PROGRAM

(71) Applicant: Seiko Epson Corporation, Tokyo (JP)

(72) Inventors: Masao Kuroda, Nagano (JP); Ichiro Aoshima, Nagano (JP); Takashi Ogiue, Nagano (JP); Tsukasa Kosuda, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 13/932,631

(22) Filed: Jul. 1, 2013

(65) Prior Publication Data

US 2013/0289418 A1    Oct. 31, 2013

Related U.S. Application Data

(63) Continuation of application No. 11/951,780, filed on Dec. 6, 2007, now Pat. No. 8,504,145.

(30) Foreign Application Priority Data

Dec. 11, 2006  (JP) ................. 2006-333190
Aug. 9, 2007  (JP) ................. 2007-207466
Nov. 29, 2007  (JP) ................. 2007-308573

(51) Int. Cl.
*A61B 5/04*     (2006.01)
(52) U.S. Cl.
USPC ....................................... 600/519

(58) Field of Classification Search
USPC .................................... 600/508, 519
See application file for complete search history.

(56) References Cited

U.S. PATENT DOCUMENTS

| | | | |
|---|---|---|---|
| 4,159,416 A | 6/1979 | Brejnik et al. | |
| 4,407,295 A | 10/1983 | Steuer et al. | |
| 4,566,461 A * | 1/1986 | Lubell et al. | 600/481 |
| 6,030,342 A | 2/2000 | Amano et al. | |
| 6,099,478 A | 8/2000 | Aoshima et al. | |
| 6,241,684 B1 * | 6/2001 | Amano et al. | 600/531 |
| 2002/0019585 A1 | 2/2002 | Dickinson | |
| 2002/0138213 A1 * | 9/2002 | Mault | 702/32 |
| 2004/0106872 A1 * | 6/2004 | Kosuda | 600/485 |
| 2006/0236748 A1 | 10/2006 | Nose et al. | |

FOREIGN PATENT DOCUMENTS

| | | |
|---|---|---|
| JP | 54-160280 A | 12/1979 |
| JP | 3250622 B2 | 1/2002 |
| JP | 2003-265448 A | 9/2003 |
| JP | 3656088 B2 | 6/2005 |

* cited by examiner

*Primary Examiner* — Christopher D Koharski
*Assistant Examiner* — Roland Dinga
(74) *Attorney, Agent, or Firm* — Global IP Counselors, LLP (57) ABSTRACT

A biometric information processing device has a heart rate detection unit that detects the heart rate of a subject; a relative heart rate calculation unit that calculates a relative heart rate, which is the relative value of the heart rate to the prescribed resting heart rate of the subject; a relative oxygen intake calculation unit that calculates a relative oxygen intake based on the relative heart rate; an oxygen intake estimation unit that estimates the oxygen intake from the relative oxygen intake; and a calorie expenditure calculation unit that calculates calorie expenditure based on the oxygen intake.

11 Claims, 9 Drawing Sheets

| DEFAULT RESTING HEART RATE HRrest ||
|---|---|
| 0 - 24 yrs | 70 BPM |
| 25 - 29 yrs | 69 BPM |
| 30 - 34 yrs | 68 BPM |
| 35 - 39 yrs | 67 BPM |
| 40 - 44 yrs | 66 BPM |
| 45 - 49 yrs | 65 BPM |
| 50 - 54 yrs | 64 BPM |
| 55 - 59 yrs | 63 BPM |
| 60 - 64 yrs | 62 BPM |
| 65 - 69 yrs | 61 BPM |
| 70 - 99 yrs | 60 BPM |

| DEFAULT MAXIMUM OXYGEN INTAKE VO2max |||
|---|---|---|
| | MALE | FEMALE |
| 0 - 19 yrs | 44 | 35 |
| 20 - 24 yrs | 43 | 34 |
| 25 - 29 yrs | 42 | 33 |
| 30 - 34 yrs | 40 | 31 |
| 35 - 39 yrs | 39 | 29 |
| 40 - 44 yrs | 37 | 28 |
| 45 - 49 yrs | 36 | 26 |
| 50 - 54 yrs | 34 | 24 |
| 55 - 59 yrs | 33 | 22 |
| 60 - 64 yrs | 31 | 21 |
| 65 - 69 yrs | 30 | 19 |
| 70 - 99 yrs | 28 | 17 |

BIOMETRIC INFORMATION PROCESSING DEVICE, BIOMETRIC INFORMATION PROCESSING METHOD, AND CONTROL PROGRAM

CROSS-REFERENCE TO THE RELATED APPLICATIONS

This is a continuation application of U.S. patent application Ser. No. 11/951,780, which claims priority to Japanese Patent Application No. 2007-308573 filed on Nov. 29, 2007. The entire disclosure of Japanese Patent Application No. 2007-308573 is hereby incorporated herein by reference.

BACKGROUND

1. Field of Invention

The present invention relates to a biometric information processing device, a biometric information processing method, and a control program, and relates more particularly to a biometric information processing device, a biometric information processing method, and a control program that estimate calorie expenditure.

2. Description of Related Art

Whether the number of calories absorbed by the body from food and drink ("calorie consumption" or "calorie intake" below) is balanced with the number or calories spent ("calorie expenditure" below) in the course of daily living is extremely important from both the perspective of personal health and preventive medicine.

The development of transportation means in modern society has, however, also tended to reduce daily calorie expenditure.

While calorie intake from food would preferably decline, calorie consumption is actually on the rise, thus disrupting the balance between calorie consumption and calorie expenditure.

This makes it important to actively exercise and increase calorie expenditure, and more and more people have begun to exercise regularly.

Exercising in order to lose or maintain weight is preferably not managed ad hoc by the individual, but according to an exercise schedule that is designed with calorie expenditure in mind.

A common method of calculating calorie expenditure through exercise for weight management is described next.

The technology taught in Japanese Unexamined Patent Appl. Pub. JP-A-S54-160280 defines a correlation curve between heart rate and calorie expenditure, and calculates calorie expenditure based on this curve simultaneously to measuring the heart rate.

The technology taught in Japanese Patent No. 3250622 stores a plurality of heart rate to calorie expenditure correlation curves, selects one of the correlation curves based on input personal data, and calculates calorie expenditure simultaneously to measuring the heart rate.

The technology taught in Japanese Patent No. 3656088 calculates calorie expenditure based on the result of determining if user activity is at the basal metabolism level, that is, whether the user is at rest.

A problem with the technology taught in JP-A-S54-160280 is that because only a single correlation curve is used, the measurements vary greatly due to individual differences when a large number of subjects are tested, and the method is therefore not applicable to multiple subjects.

Compared with the technology taught in JP-A-S54-160280, the technology taught in Japanese Patent No. 3250622 uses multiple correlation curves and can therefore be used with numerous subjects, but storing a large number of correlation curves is difficult and there are therefore practical limits to its use.

The technology taught in Japanese Patent No. 3656088 requires a means of determining if the user is at the basal metabolism level, and this complicates the design and operation.

SUMMARY

A biometric information processing device, a biometric information processing method, and a control program according to the present invention can be used to calculate calorie expenditure for many different subjects while also simplifying device design and construction.

A biometric information processing device according to one aspect of the invention has a heart rate detection unit that detects the heart rate of a subject; a relative heart rate calculation unit that calculates a relative heart rate, which is the relative value of the heart rate to the prescribed resting heart rate of the subject; a relative oxygen intake calculation unit that calculates a relative oxygen intake based on the relative heart rate; an oxygen intake estimation unit that estimates the oxygen intake from the relative oxygen intake; and a calorie expenditure calculation unit that calculates calorie expenditure based on the oxygen intake.

The heart rate detection unit detects the heart rate of the subject.

The relative heart rate calculation unit calculates the relative heart rate, which is the detected heart rate relative to the prescribed resting heart rate of the subject.

The relative oxygen intake calculation unit calculates the relative oxygen intake based on the relative heart rate.

The oxygen intake estimation unit estimates the oxygen intake from the relative oxygen intake.

Based on these results, the calorie expenditure calculation unit calculates calorie expenditure based on the oxygen intake.

The resting heart rate is the value of the resting heart rate measured in a prescribed resting state before the start of exercise, or a value input externally by the user, or a value obtained by referencing a predefined table that stores correlations between age and the resting heart rate.

When RHRmax is the relative heart rate, $RVO_2max$ is the relative oxygen intake, a is the slope of the approximation curve representing the relationship between the experimentally determined relative heart rate RHRmax and the relative oxygen intake $RVO_2max$, and b is the intercept of the approximation curve with the axis corresponding to the relative heart rate RHRmax, the relative oxygen intake calculation unit calculates relative oxygen intake $RVO_2max$ from equation (1)

$$RVO_2\text{max}=(RHR\text{max}-b)/a \quad (1)$$

when (A) the relative heart rate RHRmax 20%, and from equation (2)

$$RVO_2\text{max}=0 \quad (2)$$

when (B) the relative heart rate RHRmax<20%.

Further preferably, when $VO_2max$ is the maximum oxygen intake, and $VO_2rest$ is the resting oxygen intake indicating the basal metabolism level, the relative oxygen intake estimation unit calculates the oxygen intake $VO_2$ from the following equation:

$$VO_2=RVO_2\text{max}*(VO_2\text{max}-VO_2\text{rest})+VO_2\text{rest}.$$

Further preferably, the maximum oxygen intake $VO_2max$ is an externally input user-defined value, or a value acquired from a predefined table that stores a correlation between the maximum oxygen intake VO$_2$max and one or more values selected from a group of values containing age, sex, and physical fitness, and including at least the age.

The biometric information processing device according to another aspect of the invention also has a calorie expenditure data storage unit that stores the calorie expenditure calculated by the calorie expenditure calculation unit as calorie expenditure data.

Further preferably, the biometric information processing device also has a communication unit that is connected to an external device over a communication network and sends the calorie data to the external device.

The biometric information processing device according to another aspect of the invention also has an activity level determination unit that determines the subject is exercising if the relative heart rate is greater than or equal to a prescribed reference relative heart rate, and the calorie expenditure calculation unit uses different operations to calculate calorie expenditure when the subject is exercising and when the subject is resting.

In the biometric information processing according to another aspect of the invention the calorie expenditure calculation unit eliminates from the calorie expenditure calculation data about the oxygen intake acquired in a prescribed heart rate range in which the heart rate is considered to fluctuate easily due to psychological effects on the user when resting.

Yet further preferably, the calorie expenditure calculation unit sets the calorie expenditure to zero when the subject is in the state of greatest rest.

The biometric information processing according to another aspect of the invention also has an activity level determination unit that determines the subject is exercising if the relative heart rate is greater than or equal to a prescribed reference relative heart rate, and the calorie expenditure calculation unit uses different operations to calculate calorie expenditure when the subject is exercising and when the subject is resting.

When the relative heart rate is less than or equal to the prescribed level (such as when relative heart rate RHR-max<20%), the heart rate can fluctuate easily due to psychological effects, meals, and physical condition, and heart rate values in this range can therefore be omitted from the calorie expenditure calculation.

In a biometric information processing device according to another aspect of the invention HR is the heart rate; HRrest is the resting heart rate; HRmax is the peak heart rate defined as a function of the age of the subject; and the relative heart rate calculation unit calculates the relative heart rate RHR using the equation $$RHR=(HR-HRrest)/(HRmax-HRrest)*100(\%).$$

Further preferably, the peak heart rate HRmax is calculated from the following equation where AGE is the age of the subject:

$$HRmax=220-AGE.$$

Another aspect of the invention is a biometric information processing method including a heart rate detection step that detects the heart rate of a subject; a relative heart rate calculation step that calculates a relative heart rate, which is the relative value of the heart rate to the prescribed resting heart rate of the subject; a relative oxygen intake calculation step that calculates a relative oxygen intake based on the relative heart rate; an oxygen intake estimation step that estimates the oxygen intake from the relative oxygen intake; a calorie expenditure calculation step that calculates calorie expenditure based on the oxygen intake; and a reporting step that reports the calculated calorie expenditure to the subject.

Another aspect of the invention is a control program for controlling by means of a computer a biometric information processing device that has a heart rate detection unit for detecting the heart rate, the control program including steps of: calculating a relative heart rate, which is the relative value of the heart rate to the prescribed resting heart rate of the subject; calculating a relative oxygen intake based on the relative heart rate; estimating the oxygen intake from the relative oxygen intake; calculating calorie expenditure based on the oxygen intake; and reporting the calculated calorie expenditure to the subject.

The invention thus enables easily and accurately calculating the calorie expenditure of the user from the heart rate of the user using a simple device without being affected by individual differences between users.

Other objects and attainments together with a fuller understanding of the invention will become apparent and appreciated by referring to the following description and claims taken in conjunction with the accompanying drawings.

DESCRIPTION OF PREFERRED EMBODIMENTS

A preferred embodiment of the present invention is described below with reference to the accompanying figures.

Figure 1:
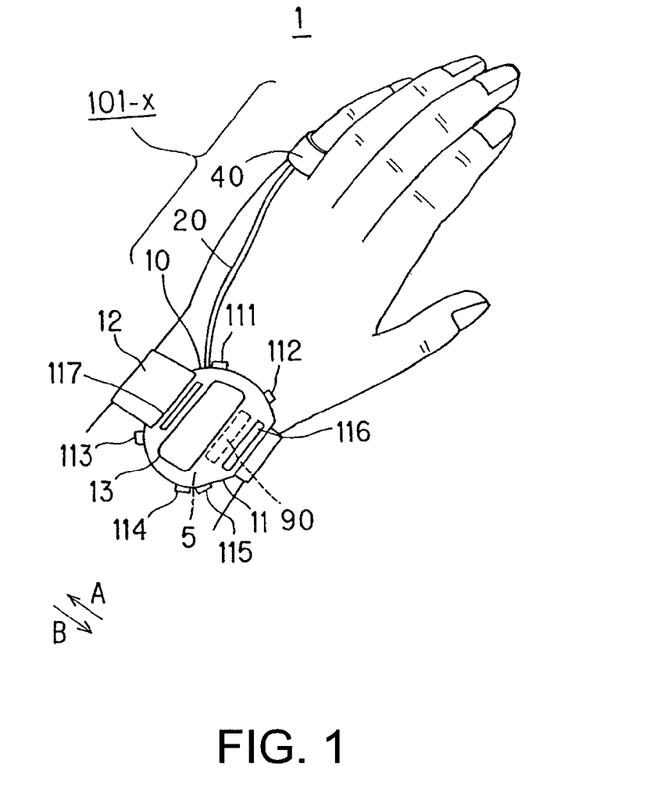
FIG. 1 describes the arrangement of a biometric information processing device according to a preferred embodiment of the invention.

FIG. 1 shows the basic arrangement of a biometric measuring instrument according to a preferred embodiment of the invention. This embodiment of the invention uses the heart rate as the biometric information of interest, detects the heart rate as the biometric data, and calculates calorie expenditure from the detected heart rate.

The biometric information processing device 1 according to this embodiment of the invention includes a wristwatch-type main unit 10, a cable 20 that is connected to this main unit 10, and a pulse sensor 30 that is disposed to the distal end of the cable 20.

A wristband 12 is attached to the main unit 10 to wrap around the wrist from the 12:00 o'clock to the 6:00 o'clock positions of a typical wristwatch. This wristband 12 holds the main unit 10 on the user's wrist so that it can be removed as desired.

Figure 2:
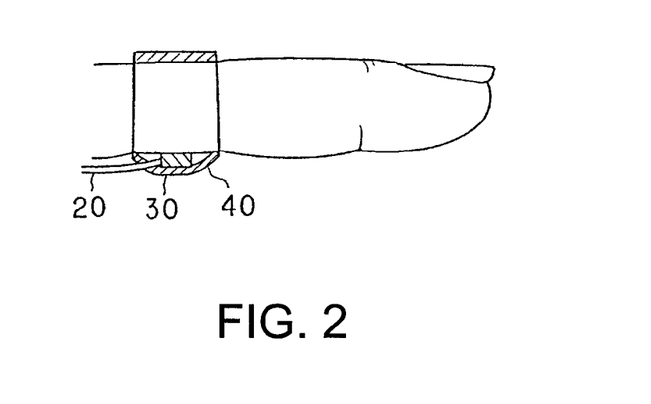
FIG. 2 is a section view of the area around the pulse sensor of the biometric information processing device.

FIG. 2 is a section view of the area around the pulse sensor 30 of the biometric information processing device.

The pulse sensor 30 is worn between the base and the first joint of the little finger shielded from light by the sensor holding band 40. Wearing the pulse sensor 30 at the base of the finger enables using a shorter cable 20 and helps keep the cable 20 from getting in the way while jogging, for example. Furthermore, when the distribution of body heat from the palm to the fingertips is measured, the drop in temperature at the base of the finger is minimal compared with the pronounced drop in temperature at the fingertips when it is cold. Wearing the pulse sensor 30 at the base of the finger thus enables accurately measuring the heart rate even when jogging outdoors on a cold day. A finger wearing the said pulse sensor 30 can not be only a little finger but also other fingers.

Figure 3:
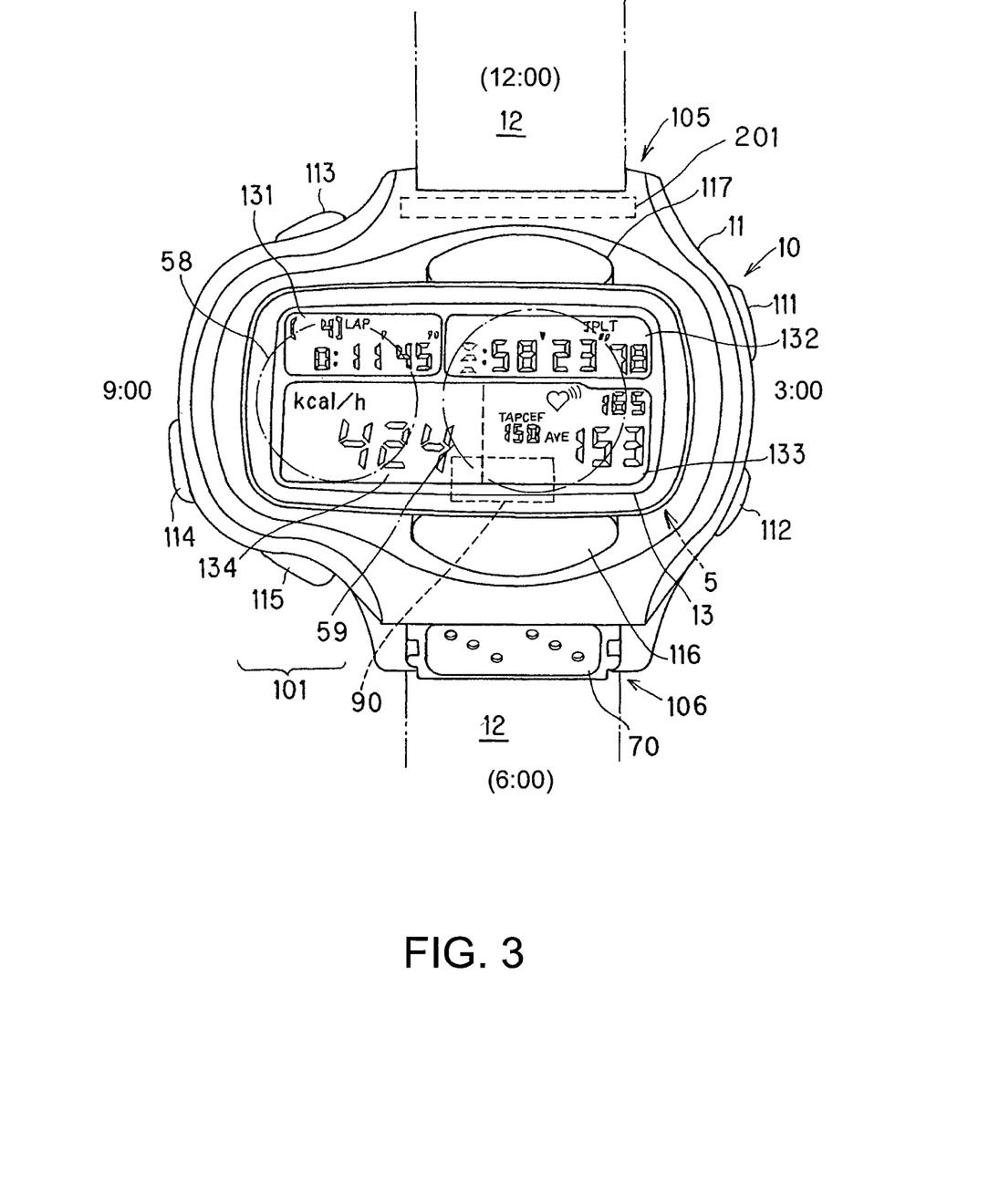
FIG. 3 is a plan view of the main unit of the biometric information processing device with the wristband and cable removed.
Figure 4:
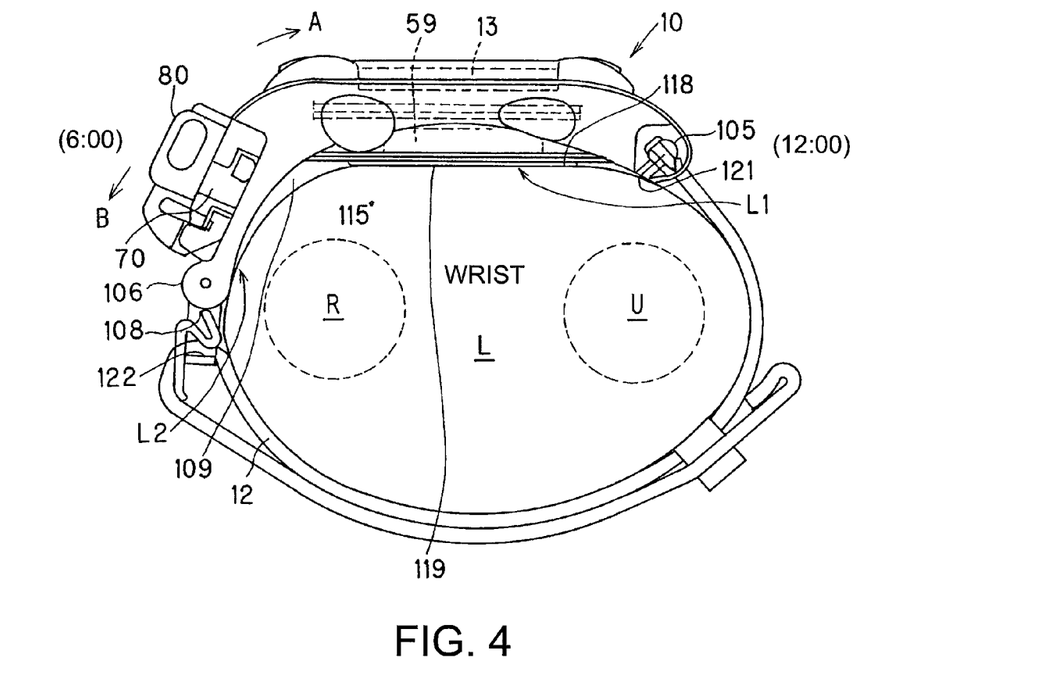
FIG. 4 is a side view of the biometric information processing device from the 3:00 o'clock side of the wristwatch.

FIG. 3 is a plan view of the main unit 10 of the biometric information processing device 1 with the wristband and cable removed. FIG. 4 is a side view of the biometric information processing device 1 from the 3:00 o'clock side of a typical wristwatch.

As shown in FIG. 3 the main unit 10 has a plastic watch case 11 (main case). A liquid crystal display (LCD) 13 (display device) with an electroluminescent backlight is disposed on the face of the watch case 11 for displaying the current time and date, the pace when walking or running, and pulse information such as the heart rate.

The LCD 13 has a first segment display area 131 located at the top left part of the display area, a second segment display area 132 at the top right, a third segment display area 133 at the bottom right, and a dot display area 134 at the bottom left. The dot display area 134 enables graphically displaying different information.

An activity sensor 302 (see FIG. 6) for determining the pace is disposed inside the watch case 11. An acceleration detector, for example, can be used as the activity sensor 302.

A control unit 5 that provides control and data processing is also disposed inside the watch case 11.

The control unit 5 calculates the heart rate and calorie expenditure based on the detection result (activity signal) output by the activity sensor 302 and the detection result (pulse wave signal) output by the pulse sensor 30, and displays the user's (subject's) calorie expenditure on the LCD 13.

The control unit 5 also has a timekeeping circuit and can also display the time on the LCD 13.

A plurality of buttons 111 to 115 for externally setting the time and changing the display mode, for example, are disposed on the outside of the watch case 11. Relatively large buttons 116 and 117 are also provided on the face of the watch case 11.

The power supply for the biometric information processing device 1 is a small button battery 59 housed inside the watch case 11. The cable 20 carries power from the battery 59 to the pulse sensor 30, and carries the detection result from the pulse sensor 30 to the control unit 5 inside the watch case 11.

As the functionality of the biometric information processing device 1 improves, the size of the main unit 10 must also increase. Because the main unit 10 is worn on the wrist, however, there is a limit to how much the size of the main unit 10 can be increased along the 6:00 to 12:00 o'clock axis of the wristwatch.

The main unit 10 according to this embodiment of the invention therefore uses a watch case 11 that is longer on the 3:00 to 9:00 o'clock axis than on the 6:00 to 12:00 o'clock axis of the wristwatch.

The wristband 12 is therefore connected at positions offset towards the 3:00 o'clock side of the watch case 11, and the watch case 11 therefore protrudes away from the wristband 12 more on the 9:00 o'clock side than on the 3:00 o'clock side. Even though the watch case 11 is thus long horizontally, the wrist can bend freely and the watch case 11 will not hit the back of the hand if, for example, the user falls down and the hand bends back.

A flat piezoelectric element 58 for a buzzer is located on the 9:00 o'clock side of the battery 59 inside the watch case 11. The center of gravity of the main unit 10 is offset to the 3:00 o'clock side because the battery 59 is heavier than the piezoelectric element 58. Because the wristband 12 is attached at the side to which the center of gravity is shifted, the main unit 10 can be held stably on the wrist. The main unit 10 can also be made thinner as a result of disposing the battery 59 and the piezoelectric element 58 side by side when seen in plan view.

A battery cover 118 is also disposed to the back cover 119 as shown in FIG. 4 so that the user can easily replace the battery 59.

As also shown in FIG. 4, lugs 105 for holding a pin 121 that is attached to the end part of the wristband 12 are formed at the 12:00 o'clock side of the watch case 11. At the 6:00 o'clock side of the watch case 11 is a receiver 106 to which a clasp 122 is attached. The wristband 12 that wraps around the wrist is folded back lengthwise around the clasp 122, which holds the folded position.

A rotation stop 108 that forms an approximately 115° angle to the back cover 119 and is formed in unison with the watch case 11 is rendered by the part from the back cover 119 to the receiver 106 at the 6:00 o'clock side of the main unit 10. More specifically, when the main unit 10 is held by the wristband 12 on the top L1 (the same side as the back of the hand) of the left wrist L, the back cover 119 of the watch case 11 is tight to the top L1 of the wrist L. The rotation stop 108 is also touching the side L2 of the radius R.

When thus positioned the back cover 119 of the main unit 10 seems to span the radius R and the ulna U, and the part from the curved part 109 extending from the rotation stop 108 to the back cover 119 to the rotation stop 108 touches the radius R. Because the angle between the rotation stop 108 and the back cover 119 is an anatomically ideal approximately 115°, the main unit 10 will not rotate unnecessarily around the arm even if the main unit 10 is rotated in the direction of arrow A or arrow B.

Rotation of the main unit 10 around the wrist is also limited by the back cover 119 and the rotation stop 108 at only two places on one side of the wrist. The back cover 119 and rotation stop 108 therefore contact even thin wrists reliably, and positively prevent the main unit 10 from rotating around the wrist. The main unit 10 also does not feel tight to a user with thick wrists.

Figure 5:
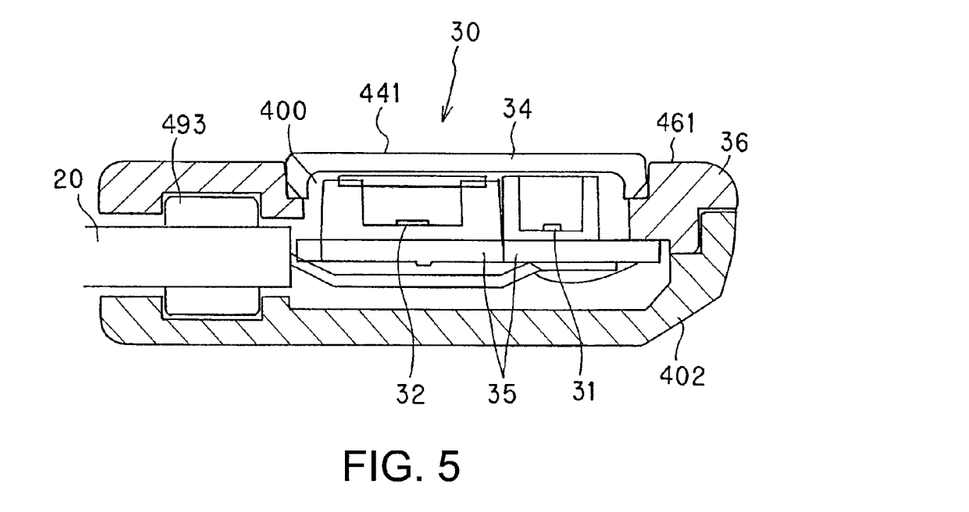
FIG. 5 is a section view of the pulse sensor in the preferred embodiment of the invention.

FIG. 5 is a section view of the pulse sensor 30 in this embodiment of the invention.

As shown in FIG. 5 the pulse sensor 30 has an internal component storage space 400 rendered by a back cover 402 covering the back of a sensor frame 36, which is the case member of the pulse sensor 30. A circuit board 35 is held inside the component storage space 400. An LED 31, a phototransistor 32, and other electronic components are mounted on the circuit board 35. The end of the cable 20 is secured by a bushing 493 to the pulse sensor 30, and the wires of the cable 20 are soldered to the wiring pattern of the circuit board 35. The pulse sensor 30 is worn on the finger so that the cable 20 extends from the base of the finger to the main unit 10. The LED 31 and the phototransistor 32 are thus disposed side by side in line with the length of the finger with the LED 31 closer to the tip of the finger and the phototransistor 32 towards the base of the finger. This arrangement has the effect of impeding the penetration of ambient light to the phototransistor 32.

The pulse sensor 30 has a light-transmitting window rendered by a transparent plate 34 made of glass in the top part (the actual pulse signal detection unit) of the sensor frame 36. The LED 31 and the phototransistor 32 are oriented to the transparent plate 34 so that the light-emitting side and the light-receiving side, respectively, are facing the transparent plate 34. As a result, the pulse sensor 30 is worn with the outside surface 441 (that is, the sensor surface, the surface that contacts the surface of the finger) of the transparent plate 34 touching the skin and the LED 31 emits light to the surface of the finger. The phototransistor 32 can also detect the light that is emitted by the LED 31 and reflected back from the finger. To promote tight contact between the outside surface 441 of the transparent plate 34 and the surface of the finger, the outside surface 441 of the transparent plate 34 protrudes above the surrounding part 461.

The LED 31 in this embodiment of the invention is an InGaN (indium-gallium-nitrogen) blue LED that has an emission spectrum with a 450-nm emission peak. The LED 31 emits light in the wavelength range from 350 nm to 600 nm. To provide an LED 31 with these emission characteristics, this embodiment of the invention uses a GaAsP (gallium-arsenic-phosphorus) phototransistor as the phototransistor 32. The primary sensitivity range of the photoreception range of the phototransistor 32 is from 300 nm to 600 nm, but the phototransistor 32 is also sensitive to wavelengths less than 300 nm.

The pulse sensor 30 is held at the base of the finger by the sensor holding band 40 so that when the LED 31 emits light to the finger and the light reaches the internal blood vessels, part of the light is absorbed by hemoglobin in the blood and part of the light is reflected. The light that is reflected by the finger (blood vessel) is received by the phototransistor 32, and the change in the amount of light received corresponds to the change in blood volume (that is, pulses of blood). More specifically, the reflected light becomes weaker when the blood volume is high, and when the blood volume is low, the reflected light is stronger. Biometric information including the heart rate can thus be measured by detecting the change in the intensity of the reflected light.

This embodiment of the invention displays biometric information based on detection results obtained from the wavelength range below approximately 700 nm, or more specifically the wavelength range from approximately 300 nm to approximately 600 nm, which is the range where the emission range of the LED 31 and the detection range of the phototransistor 32 overlap.

The reason this arrangement is used is that if ambient light contacts the exposed part of the finger, light in the wavelength range below approximately 700 nm that is contained in the ambient light will not reach the phototransistor 32 (photoreception unit) using the finger as a light conductor. This is because it is difficult for light in the wavelength range below approximately 700 nm that is contained in the ambient light to pass through the finger. Therefore, ambient light contacting the part of the finger that is not covered by the sensor holding band 40 will therefore not travel through the finger to the phototransistor 32, and will therefore not affect the detection result.

Furthermore, because the pulse information is acquired using light in the wavelength range below approximately 700 nm, the S/N ratio of the pulse signal based on the change in blood volume is high. This is because the light absorption coefficient of hemoglobin in the blood to light with a wavelength from 300 nm to 700 nm is from several times to approximately 100 times greater than the absorption coefficient to light at the conventional detection beam wavelength of 880 nm. The pulse detection rate (SNR) based on change in blood volume is therefore increased because signal output changes with good sensitivity to the change in blood volume.

Figure 6:
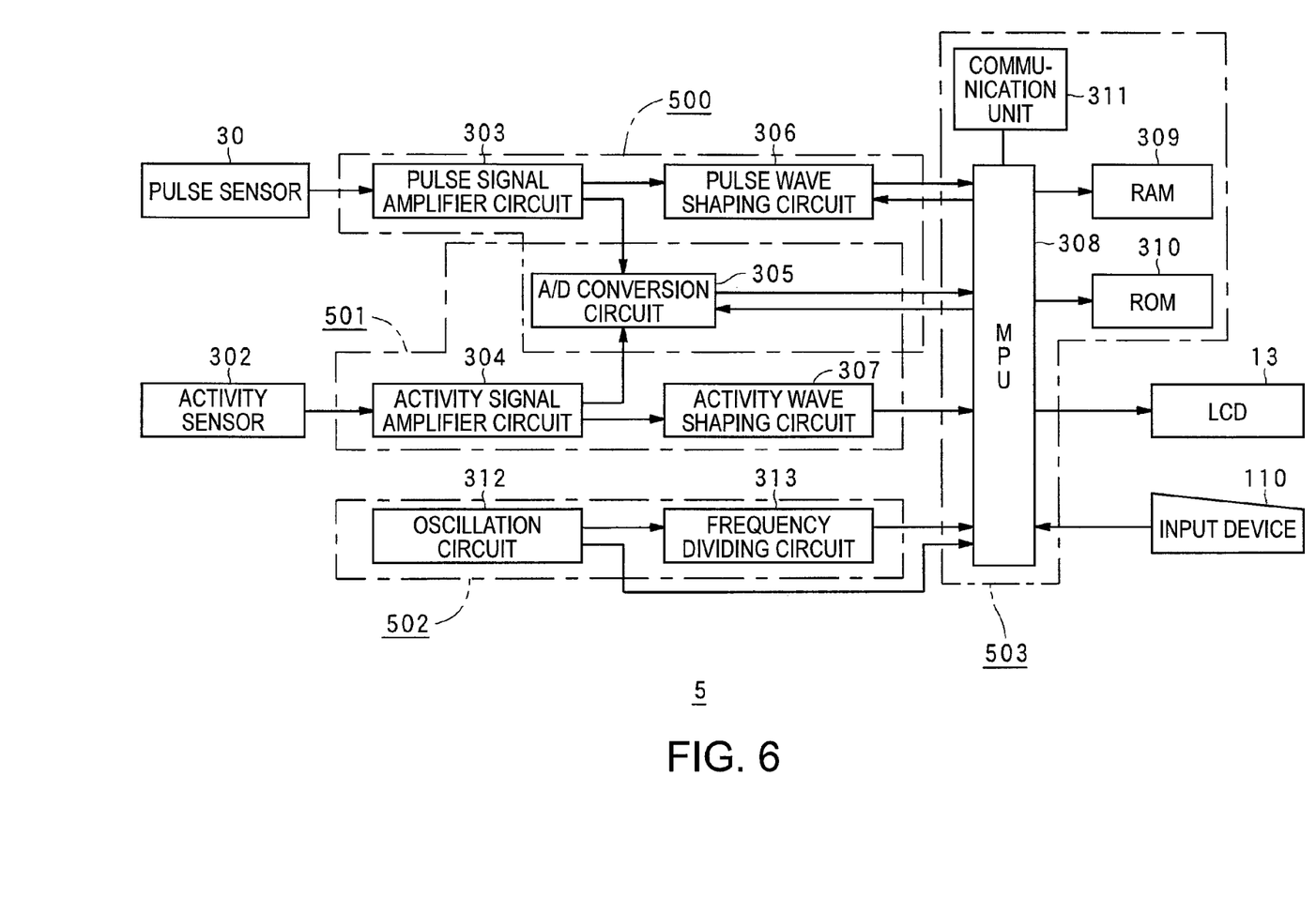
FIG. 6 is a block diagram of the components related to the control unit.

FIG. 6 is a schematic block diagram of the area around the control unit.

The control unit 5 includes a pulse data processing unit 500 for determining the heart rate based on input from the pulse sensor 30, a pitch data processing unit 501 for determining the pitch based on input from the activity sensor 302, a clock generator 502 for generating an operating clock signal, and a control section 503 for controlling the control unit 5.

The pulse data processing unit 500 includes a pulse signal amplifier circuit 303 and a pulse wave shaping circuit 306, and an A/D conversion circuit 305 that is shared with the pitch data processing unit 501.

The pulse signal amplifier circuit 303 amplifies the pulse signal output by the pulse sensor 30 and outputs the pulse amplification signal to the A/D conversion circuit 305 and the pulse wave shaping circuit 306.

The pulse wave shaping circuit 306 shapes the pulse amplification signal and outputs to the control section 503.

The A/D conversion circuit 305 A/D converts the pulse amplification signal and outputs the resulting pulse data to the control section 503.

The pitch data processing unit 501 includes a activity signal amplifier circuit 304 and a activity wave shaping circuit 307, and shares the A/D conversion circuit 305 with the pulse data processing unit 500 as noted above.

The activity signal amplifier circuit 304 amplifies the activity signal output by the activity sensor 302, and outputs the activity amplification signal to the A/D conversion circuit 305 and the activity wave shaping circuit 307.

The activity wave shaping circuit 307 shapes the activity amplification signal and outputs to the control section 503.

The A/D conversion circuit 305 A/D converts the activity amplification signal and outputs the resulting activity data to the control section 503.

The clock generator 502 includes an oscillation circuit 312 and a frequency dividing circuit 313.

The oscillation circuit 312 includes a crystal oscillator, supplies a clock signal to the control section 503 as the reference operating clock, and to the frequency dividing circuit 313 which generates a clock signal for timekeeping from the clock signal.

The frequency dividing circuit 313 frequency divides the supplied clock signal and generates and supplies clock signals for timekeeping to the control section 503.

The control section 503 includes an MPU 308, RAM 309, ROM 310, and a communication unit 311.

The MPU 308 controls the control unit 5, and therefore the biometric information processing device 1, based on a control program stored in the ROM 310.

The RAM 309 temporarily stores data including the pulse data and activity data, and is used as working memory.

The ROM 310 stores the control program that controls operation of the MPU 308 and thereby the biometric information processing device 1.

The communication unit 311 is controlled by the MPU 308 and handles data communication with connected external devices through a communication connector. More specifically, the communication unit 311 outputs measurement data to the external device and enables inputting configuration data for the biometric information processing device 1 from an external device.

Before describing the operation for calculating calorie expenditure, the calorie expenditure calculation method used in this embodiment of the invention is described first below.

Use of this embodiment of the invention presumes that certain conditions such as described below are true.

This embodiment of the invention calculates calorie expenditure from oxygen intake, and the heart rate is within a range that varies proportionally to the intensity of the exercise (activity).

When the heart rate is low or high, the heart rate may not vary proportionally to the exercise level due, for example, to psychological effects on the heart rate when the activity level is low, causing the heart rate to rise above the oxygen intake limit.

There are individual differences in the heart rate due to age, sex, and physical fitness.

The resting heart rate as used below is the lowest heart rate measured when the user is sitting at rest before measurement starts and the heart rate is stable.

The relationship between the relative heart rate and the relative oxygen intake is described next.

Figure 7:
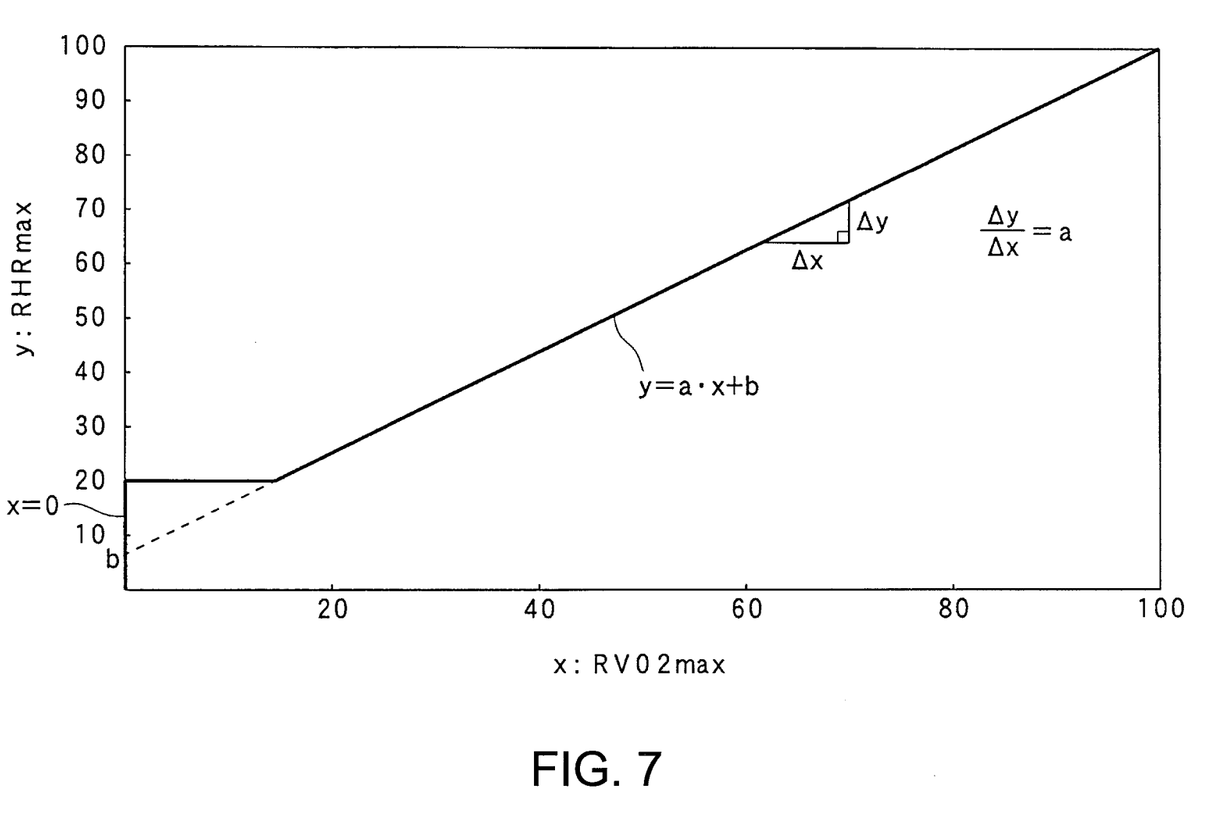
FIG. 7 describes the relationship between the relative heart rate and relative oxygen intake in the preferred embodiment of the invention.

FIG. 7 is a graph describing the relationship between the relative heart rate and the relative oxygen intake in this embodiment of the invention.

In this embodiment of the invention the relative heart rate $RHRmax$ is calculated from equation (1) where HR is the subject's (user's) heart rate, HRrest is the resting heart rate, which is the heart rate of the subject at rest, and HRmax is the peak heart rate defined as a function of the age of the subject (user).

$$RHR=(HR-HRrest)/(HRmax-HRrest)*100[\%] \quad (1)$$

In equation (1) the peak heart rate HRmax is defined by equation (2).

$$HRmax=220-AGE$$

where AGE is the age of the subject.

As shown in FIG. 7 the relative oxygen intake $RVO_2max$ is calculated differently when the relative heart rate $RHRmax$ is greater than or equal to 20% and when the relative heart rate $RHRmax$ is less than 20%, that is, when the exercise load is high and low.

A threshold value used by way of example in this embodiment is called the anaerobic threshold AT.

The anaerobic threshold AT is the oxygen intake $VO_2$ at the point where anaerobic metabolism starts in addition to aerobic metabolism, and is the maximum exercise level that can be sustained for an extended time with relative safety.

More specifically, when the relative heart rate $RHRmax$ is greater than or equal to 20% (the exercise load is high), "a" is the slope of the approximation curve y representing the relationship between the experimentally determined relative heart rate $RHRmax$ (y axis) and the relative oxygen intake $RVO_2max$ (x axis), and "b" is the intercept of the approximation curve y with the axis (y axis) corresponding to the relative heart rate $RHRmax$, the relative oxygen intake $RVO_2max$ is calculated from equation (3). When the relative heart rate $RHRmax$ is less than 20% (the exercise load is low), relative oxygen intake $RVO_2max$ is calculated from equation (4).

$$RVO_2max=(RHRmax-b)/a \quad (3)$$

$$RVO_2max=0 \quad (4)$$

This is because when the relative heart rate $RHRmax$ is low the reliability of the heart rate is low and error is thus high. However, because the effect on calculating the relative oxygen intake $RVO_2max$ is not great even if the error in the relative heart rate $RHRmax$ is somewhat high in this range, the experimentally determined equation (4) is defined as an easy to use equation.

The relationship between relative oxygen intake $RVO_2max$ and oxygen intake $VO_2$ is described next.

In this embodiment of the invention oxygen intake $VO_2$ is defined by equation (5) where $VO_2max$ is the maximum oxygen intake and $VO_2rest$ is the resting oxygen intake indicating the basal metabolism level. The maximum oxygen intake $VO_2max$ is input and set by the user through the input device 110.

$$VO_2=RVO_2max*(VO_2max-VO_2rest)+VO_2rest \quad (5)$$

Note that the resting oxygen intake $VO_2rest$ is obtained using the Harris-Benedict equations.

More specifically, the resting oxygen intake $VO_2rest$ per day is defined by sex using the following equations where W is weight, T is height, and AGE is the subject's age.

Male: $VO_2rest=66.47+(13.75*W)+(5.0*T)-(6.76*AGE)$

Female: $VO_2rest=66.51+(9.56*W)+(1.85*T)-(4.68*AGE)$

Because the resting oxygen intake $VO_2rest$ obtained by these equations is the oxygen intake per day, this value is converted to the resting oxygen intake $VO_2rest$ per minute to calculate the actual calorie expenditure. More specifically, the result is multiplied by $1/(24*60)$.

Based on the weight W of the user (subject), calorie expenditure C (kcal/min) is calculated from the oxygen intake $VO_2$ (ml/kg/min).

More specifically, calorie expenditure C is calculated from equation (6) where calorie expenditure per liter of oxygen intake is 5 kcal and t is the sustained heart rate time corresponding to the same oxygen intake $VO_2$.

$$C=VO_2*W*5*t \quad (6)$$

The operation of this embodiment of the invention based on the above equations is described next.

Figure 8:
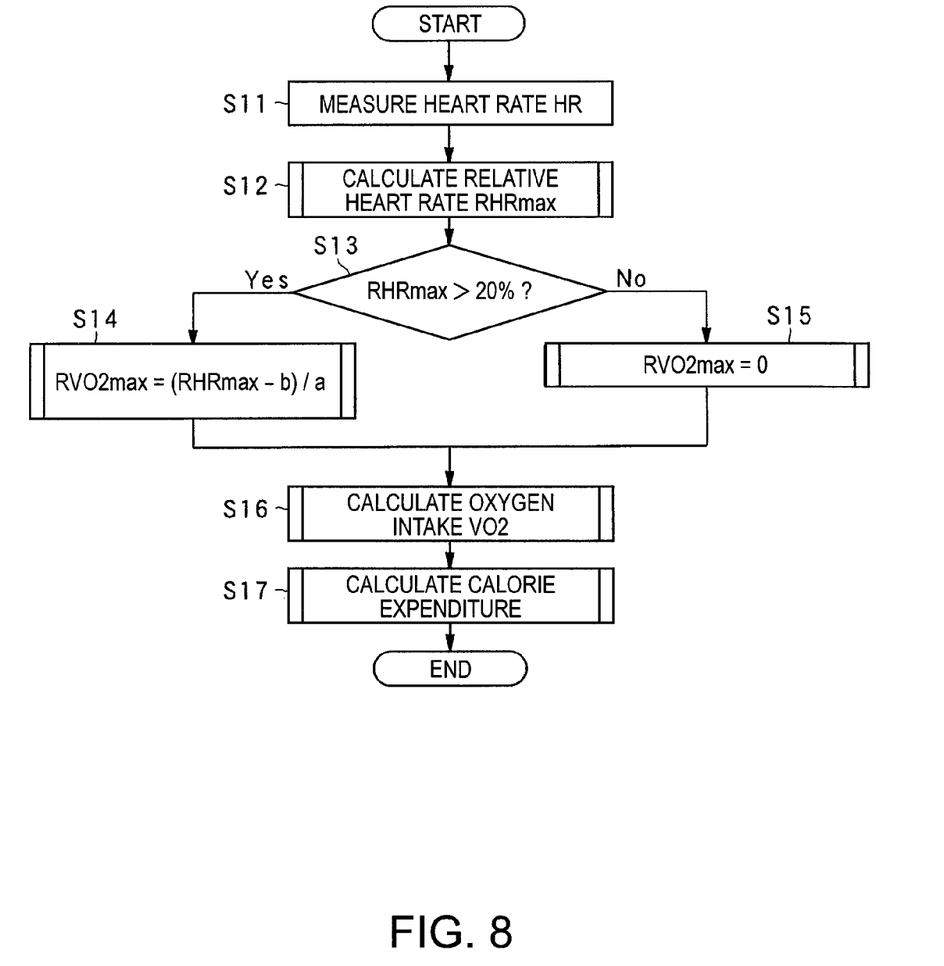
FIG. 8 is a flow chart of the calorie expenditure calculation process of the biometric information processing device according to the preferred embodiment of the invention.

FIG. 8 is a flow chart of the calorie expenditure calculation process of the biometric information processing device according to this embodiment of the invention.

The MPU 308 of the biometric information processing device 1 first measures the heart rate HR (step S11).

Measuring the heart rate HR is described in detail first.

The MPU 308 first gets the output signals from the pulse sensor 30 and the activity sensor 302.

More specifically, the pulse sensor 30 detects the pulse of the user, and outputs the detected pulse signal to the pulse signal amplifier circuit 303. The pulse signal amplifier circuit 303 amplifies the input pulse signal and outputs to the A/D conversion circuit 305 and the pulse wave shaping circuit 306. The pulse wave shaping circuit 306 shapes the pulse signal and outputs to the MPU 308.

The activity sensor 302 detects user activity and outputs the detected activity signal to the activity signal amplifier circuit 304. The activity signal amplifier circuit 304 amplifies the activity signal and outputs to the A/D conversion circuit 305 and the activity wave shaping circuit 307. The activity wave shaping circuit 307 then shapes the activity signal and outputs to the MPU 308.

As a result, the A/D conversion circuit 305 A/D converts the pulse signal and the activity signal, and outputs the result as the pulse data and activity data to the MPU 308.

The MPU 308 then applies a fast Fourier transformation (FFT) to the pulse data and the activity data, and extracts the heart rate component Fm and the activity component Ft from the result of the fast Fourier transformation of the pulse data and the activity data.

The MPU 308 then determines if the activity component is greater than a prescribed threshold value for determining if the heart rate can be calculated.

If the activity component is greater than the prescribed threshold value for determining if the heart rate can be calculated, the activity component is too large to calculate the heart rate, and the current heart rate cannot be measured.

However, if the activity component is less than or equal to the prescribed threshold value for determining if the heart rate can be calculated, the activity component is subtracted from the heart rate component. More specifically, $$Fm=Fm-Ft.$$

That is, the frequency component that is present only in the pulse signal is extracted.

The maximum frequency component in the extracted heart rate component Fm is used as the heart rate spectrum.

Based on the frequency of the extracted heart rate spectrum, the MPU 308 then calculates the heart rate HR.

The MPU 308 then calculates the relative heart rate RHRmax from equations (1) and (2) described above (step S12). More specifically, relative heart rate RHRmax is calculated from the following equation.

$$RHRmax=(HR-HRrest)/(HRmax-HRrest)*100$$

The MPU 308 then determines if the calculated relative heart rate RHRmax is greater than 20(%) (step S13).

If the MPU 308 decides in step S13 that the calculated relative heart rate RHRmax is greater than 20(%), that is, the exercise load is high (step S13 returns Yes), the MPU 308 calculates the relative oxygen intake $RVO_2max$ from equation (3) described above (step S14), and control goes to step S16.

If the MPU 308 decides in step S13 that the calculated relative heart rate RHRmax is less than or equal to 20(%), that is, the exercise load is low (step S13 returns No), the MPU 308 calculates the relative oxygen intake $RVO_2max$ from equation (4) described above (step S15), and control goes to step S16.

The MPU 308 then estimates the current oxygen intake $VO_2$ from equation (5) (step S16).

When estimating the current oxygen intake $VO_2$ from equation (5), the MPU 308 calculates the resting oxygen intake $VO_2rest$ (=basal metabolic rate) using the Harris-Benedict equations as noted above.

Then based on the calculated resting oxygen intake $VO_2rest$ the MPU 308 calculates the current oxygen intake $VO_2$ from the following equation.

$$VO_2=RVO_2max*(VO_2max-VO_2rest)+VO_2rest$$

The MPU 308 then calculates the calorie expenditure C from the current oxygen intake $VO_2$ (step S17).

More specifically, the calorie expenditure C is calculated from equation (6) described above.

$$C=VO_2V*W*5*t$$

Assuming that the same level of exercise continues for one hour, the total calorie expenditure CT is then calculated as $$CT=C*60$$

and the calculated result, that is, total calorie expenditure CT (kcal/h) is displayed on the LCD 13 as shown in FIG. 3.

As described above, this embodiment of the invention automatically calculates calorie expenditure from exercising based on the heart rate. As a result, the user can easily know how many calories are being burned when exercising without having specialized knowledge or requiring complex, expensive equipment.

The size and cost of the device can also be reduced because calorie expenditure can be calculated by a simple operation if the heart rate can be measured.

Furthermore, because the relative oxygen intake is used to calculate the calorie expenditure, the calorie expenditure can be calculated with little error as a result of considering individual differences, particularly differences in physical fitness.

Figure 9:
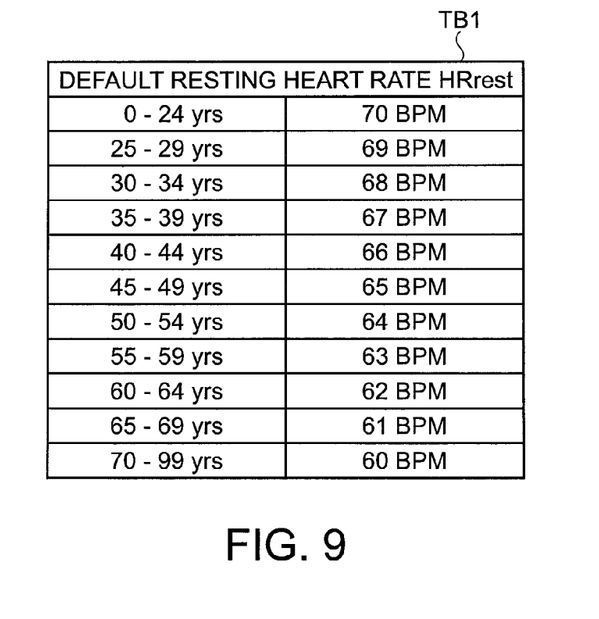
FIG. 9 is a table showing the correlation between age and the heart rate HRrest at rest.

FIG. 9 is a table showing the correlation between age and the resting heart rate HRrest.

The user sets the resting heart rate HRrest in the example described above. As shown in FIG. 9, however, an age to resting heart rate HRrest correlation table TB1 can be stored in memory, and the age to resting heart rate HRrest correlation table TB1 can be referenced to set the resting heart rate HRrest based on the input age. According to the embodiment, a user can easily acquire the measurement result that is nearer to a result from the real resting heart rate HR rest even when a user does not know his or her resting heart rate HR rest.

Figure 10:
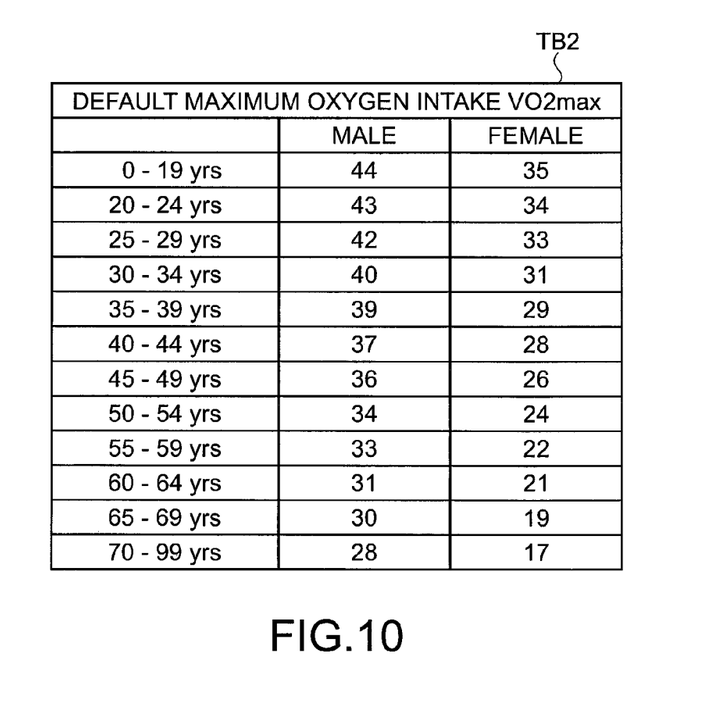
FIG. 10 is a table showing the correlation between age and maximum oxygen intake by sex.

FIG. 10 is a table correlating age and sex to the maximum oxygen intake.

The user uses the input device 110 to set the maximum oxygen intake $VO_2max$ in the example described above. As shown in FIG. 10, however, an age/sex to maximum oxygen intake correlation table TB2 can be stored in memory, and the age/sex to maximum oxygen intake correlation table TB2 can be referenced to set the maximum oxygen intake $VO_2max$ based on the input age and sex of the user. According to the embodiment, a user can easily acquire more accurate measurement result even when a user does not know his or her maximum oxygen intake VO2max.

It is also possible to measure the heart rate while the user (subject) performs a program producing a specific exercise load, and determine and set the maximum oxygen intake $VO_2max$ of the user based on the relationship between the predetermined heart rate and maximum oxygen intake $VO_2max$. According to the embodiment, it enables the device to measure more accurate amount of maximum oxygen intake by VO2max for a user compared to circumstances when the user inputs a certain amount by himself or herself or when the user sets an amount on the basis of his or her age and sex when the user does not know his or her maximum oxygen intake VO2max.

The calculation process changes in the operation described above based on whether or not the relative heart rate RHRmax is greater than or equal to 20%. However, because the heart rate tends to fluctuate easily due to psychological effects, eating, and physical condition when the relative heart rate RHRmax is less than or equal to a prescribed level (such as less than 20%), it is also possible to not use the data for calculating the calorie expenditure.

The control program for controlling the biometric information processing device is stored in ROM in the embodiment described above, but the control program can alternatively be recorded to magnetic disk, optical disc, a memory card, or other recording medium, and the program can be read in and installed from the recording medium as needed. A communication interface can also be provided so that the control program can be downloaded and installed from a communication network such as the Internet or a LAN.

Examples

Specific examples of calculating calorie expenditure are described below.

As described above, calorie expenditure is calculated from oxygen intake in the following examples, and it is assumed that the heart rate is within the range of varying proportionally to the intensity of the activity (exercise), there are situations when the heart rate is low or high that the heart rate does not vary proportionally to the intensity of the activity, and there are individual differences in the heart rate due to age, sex, and physical fitness.

The correlation between the relative heart rate and the relative oxygen intake is described first.

The measurement conditions for the tests in this example are as follow.

There were approximately ten subjects ranging in age from 10 years to 40 years.

To determine the relationship between the relative heart rate and the relative oxygen intake, the heart rate was measured using the biometric information processing device described above, and test data was acquired using a common respiratory metabolism measuring device that enables load control.

To determine the resting heart rate, a warm-up period was provided before measurement started, and the heart rate was automatically measured when the pulse stabilized in the warm-up period (more specifically, approximately 10 minutes after the start of the warm up period).

Figure 11:
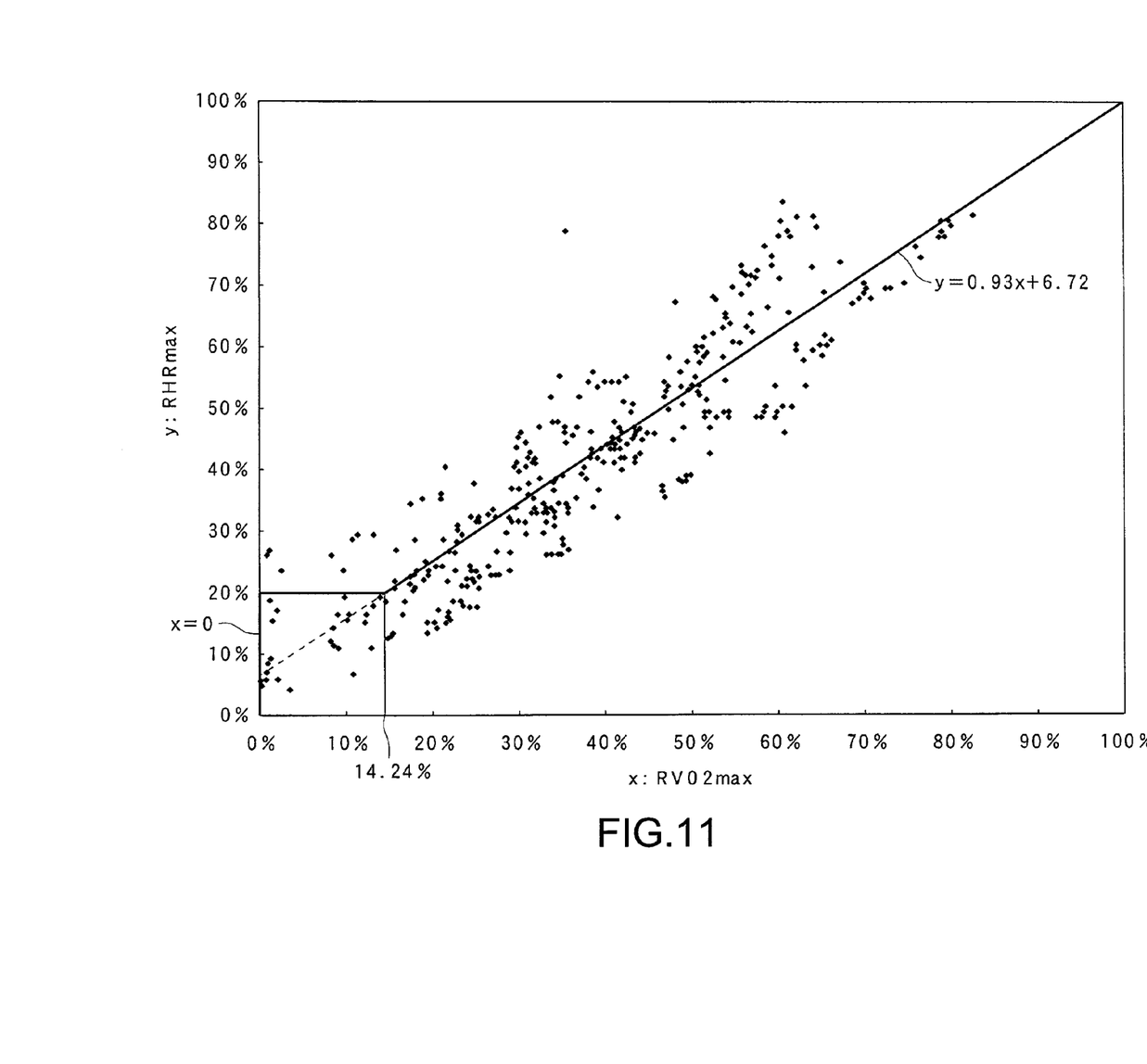
FIG. 11 is a graph showing the correlation between the relative heart rate and relative oxygen intake in the preferred embodiment of the invention.

FIG. 11 is a graph showing the relationship between the relative heart rate and the relative oxygen intake.

In this example the relative heart rate RHRmax is calculated from equation (6) where HR is the subject's (user's) heart rate, HRrest is the resting heart rate, which is the heart rate of the subject at rest, and HRmax is the peak heart rate defined as a function of the age of the subject (user).

$$RHR=(HR-HRrest)/(HRmax-HRrest)*100[\%] \quad (6)$$

In equation (7) the peak heart rate HRmax is defined by equation (7).

$$HRmax=220-AGE \quad (8)$$

where AGE is the age of the subject.

As shown in FIG. 11 the relative oxygen intake $RVO_2max$ is calculated differently when the relative heart rate RHRmax is greater than or equal to 20% and when the relative heart rate RHRmax is less than 20%, that is, when the exercise load is high and low.

A threshold value used by way of example in this embodiment is called the anaerobic threshold AT.

The anaerobic threshold AT is the oxygen intake $VO_2$ at the point where anaerobic metabolism starts in addition to aerobic metabolism, and is the maximum exercise level that can be sustained for an extended time with relative safety.

More specifically, when the relative heart rate RHRmax is greater than or equal to 20% (the exercise load is high), the relative oxygen intake $RVO_2max$ is calculated from equation (9). When the relative heart rate RHRmax is less than 20% (the exercise load is low), relative oxygen intake $RVO_2max$ is calculated from equation (10).

$$RVO_2max=(RHRmax-6.72)/0.93 \quad (9)$$

$$RVO_2max=0 \quad (10)$$

This is because when the relative heart rate RHRmax is low the reliability of the heart rate is low and error is thus high. However, because the effect on calculating the relative oxygen intake $RVO_2max$ is not great even if the error in the relative heart rate RHRmax is somewhat high in this range, the experimentally determined equation (9) is defined as an easy to use equation.

The relationship between relative oxygen intake $RVO_2max$ and oxygen intake $VO_2$ is described next.

In this embodiment of the invention oxygen intake $VO_2$ is defined by equation (11) where $VO_2max$ is the maximum oxygen intake and $VO_2rest$ is the resting oxygen intake indicating the basal metabolism level. The maximum oxygen intake $VO_2max$ is input and set by the user through the input device 110.

$$VO_2=RVO_2max*(VO_2max-VO_2rest)+VO_2rest \quad (11)$$

Note that the resting oxygen intake $VO_2rest$ in equation (10) is obtained using the Harris-Benedict equations.

More specifically, the resting oxygen intake $VO_2rest$ per day is defined by sex using the following equations where W is weight, T is height, and AGE is the subject's age.

Male: $VO_2rest=66.47+(13.75*W)+(5.0*T)-(6.76*AGE)$

Female: $VO_2rest=66.51+(9.56*W)+(1.85*T)-(4.68*AGE)$

Because the resting oxygen intake $VO_2rest$ obtained by these equations is the oxygen intake per day, this value is converted to the resting oxygen intake $VO_2rest$ per minute to calculate the actual calorie expenditure. More specifically, the result is multiplied by $1/(24*60)$.

Based on the weight W of the user (subject), calorie expenditure C (kcal/min) is calculated from the oxygen intake $VO_2$ (ml/kg/min).

More specifically, calorie expenditure C is calculated from equation (6) where calorie expenditure per liter of oxygen intake is 5 kcal and t is the sustained heart rate time corresponding to the same oxygen intake $VO_2$.

$$C=VO_2*W*5*t \quad (12)$$

The operation of this embodiment of the invention based on the above equations is described next.

Figure 12:
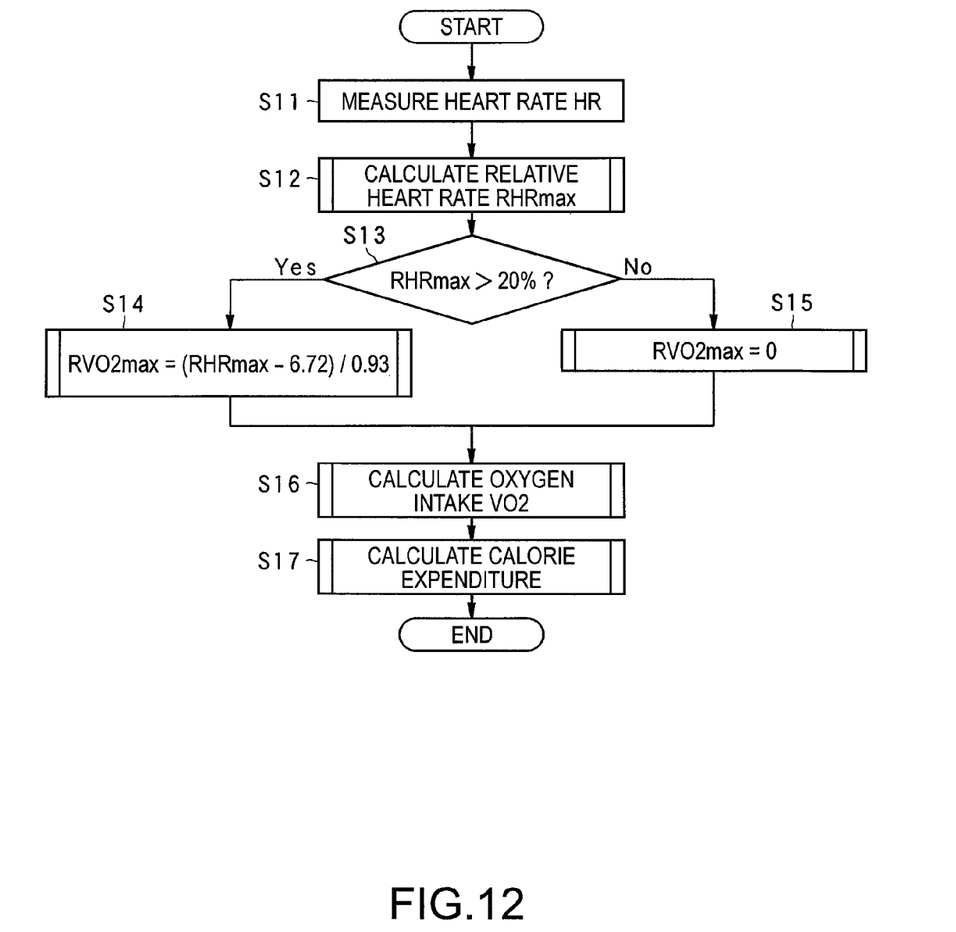
FIG. 12 is a flow chart describing the calorie expenditure calculation of the biometric information processing device according to the preferred embodiment of the invention.

FIG. 12 is a flow chart of the calorie expenditure calculation process of the biometric information processing device according to this aspect of the invention.

The MPU 308 of the biometric information processing device 1 first measures the heart rate HR (step S11).

Measuring the heart rate HR is described in detail first.

The MPU 308 first gets the output signals from the pulse sensor 30 and the activity sensor 302.

More specifically, the pulse sensor 30 detects the pulse of the user, and outputs the detected pulse signal to the pulse signal amplifier circuit 303. The pulse signal amplifier circuit 303 amplifies the input pulse signal and outputs to the A/D conversion circuit 305 and the pulse wave shaping circuit 306. The pulse wave shaping circuit 306 shapes the pulse signal and outputs to the MPU 308.

The activity sensor 302 detects user activity and outputs the detected activity signal to the activity signal amplifier circuit 304. The activity signal amplifier circuit 304 amplifies the activity signal and outputs to the A/D conversion circuit 305 and the activity wave shaping circuit 307. The activity wave shaping circuit 307 then shapes the activity signal and outputs to the MPU 308.

As a result, the A/D conversion circuit 305 A/D converts the pulse signal and the activity signal, and outputs the result as the pulse data and activity data to the MPU 308.

The MPU 308 then applies a fast Fourier transformation (FFT) to the pulse data and the activity data, and extracts the heart rate component Fm and the activity component Ft from the result of the fast Fourier transformation of the pulse data and the activity data.

The MPU 308 then determines if the activity component is greater than a prescribed threshold value for determining if the heart rate can be calculated.

If the activity component is greater than the prescribed threshold value for determining if the heart rate can be calculated, the activity component is too large to calculate the heart rate, and the current heart rate cannot be measured.

However, if the activity component is less than or equal to the prescribed threshold value for determining if the heart rate can be calculated, the activity component is subtracted from the heart rate component. Proper heart rate component Fm is defined as removing the activity component Ft from the heart rate component Fm. More specifically, $$Fm = Fm - Ft.$$

That is, the frequency component that is present only in the pulse signal is extracted.

The maximum frequency component in the extracted heart rate component Fm is used as the heart rate spectrum.

Based on the frequency of the extracted heart rate spectrum, the MPU 308 then calculates the heart rate HR.

The MPU 308 then calculates the relative heart rate RHRmax from equations (6) and (7) described above (step S12). More specifically, relative heart rate RHRmax is calculated as follows where the measured heart rate HR is 140 pulses/min, the age AGE is 40 (years), and the user-defined resting heart rate HRrest is 60 pulses/min.

$$RHRmax = (HR - HRrest)/(HRmax - HRrest) * 100$$
$$= (140 - 60)/\{(220 - 40) - 60\} * 100$$
$$= 66.7\ (\%)$$

The MPU 308 then determines if the calculated relative heart rate RHRmax is greater than 40(%) (step S13).

If the MPU 308 decides in step S13 that the calculated relative heart rate RHRmax is greater than 20(%), that is, the exercise load is high (step S13 returns Yes), the MPU 308 calculates the relative oxygen intake $RVO_2max$ from equation (8) described above (step S14), and control goes to step S16.

If the MPU 308 decides in step S13 that the calculated relative heart rate RHRmax is less than or equal to 20(%), that is, the exercise load is low (step S13 returns No), the MPU 308 calculates the relative oxygen intake $RVO_2max$ from equation (10) described above (step S15), and control goes to step S16.

Because the relative heart rate RHRmax is 66.7(%) in this example, the relative oxygen intake $RVO_2max$ is calculated from the foregoing equation (9). As a result, $$RVO_2max = (66.7 - 6.72)/0.93$$
$$= 64.5\ (\%)$$

The MPU 308 then estimates the current oxygen intake $VO_2$ from equation (11) (step S16).

When estimating the current oxygen intake $VO_2$ from equation (5), the MPU 308 calculates the resting oxygen intake $VO_2rest$ (=basal metabolic rate) using the Harris-Benedict equations as noted above.

If the subject is male, height T=173 cm, and weight W=65 kg, then:

$$VO_2rest = 66.47 + (13.75 * W) + (5.0 * T) - (6.76 * AGE)$$
$$= 66.47 + (13.75 * 65) + (5.0 * 173) - (6.76 * 40)$$
$$= 1554.8\ \text{kcal/day}$$

Therefore, if calorie expenditure per liter of oxygen intake is 5 kcal, the resting oxygen intake $VO_2rest$ per minute per kilogram of body weight is $$VO_2rest = 1554.8/24/60 * 100/5/65$$
$$= 3.322\ (\text{ml/kg/min}).$$

The current oxygen intake $VO_2$ is therefore as follows.

$$VO_2 = RVO_2max * (VO_2max - VO_2rest) + VO_2rest$$
$$= 0.645 * (40 - 3.322) + 3.322$$
$$= 27.0\ (\text{ml/kg/min})$$

The MPU 308 then calculates the calorie expenditure C from the current oxygen intake $VO_2$ (step S17).

More specifically, the calorie expenditure C is calculated from equation (6) described above.

$$C = VO_2V * W * 5 * t$$
$$= 27.0 * 65 * 5 * 1$$
$$= 8.8\ (\text{kcal/min})$$

Assuming that the same level of exercise continues for one hour, the total calorie expenditure CT is then calculated as $$CT = C * 60$$
$$= 528.0\ (\text{kcal/h})$$

and the calculated result, that is, total calorie expenditure CT=424 kcal/h is displayed on the LCD 13 as shown in FIG. 3.

As described above, this embodiment of the invention automatically calculates calorie expenditure from exercising based on the heart rate. As a result, the user can easily know how many calories are being burned when exercising without having specialized knowledge or requiring complex, expensive equipment.

The size and cost of the device can also be reduced because calorie expenditure can be calculated by a simple operation if the heart rate can be measured.

Furthermore, because the relative oxygen intake is used to calculate the calorie expenditure, the calorie expenditure can be calculated with little error as a result of considering individual differences, particularly differences in physical fitness.

FIG. 9 is a table showing the correlation between age and the resting heart rate HRrest.

The user sets the resting heart rate HRrest in the example described above. As shown in FIG. 9, however, an age to resting heart rate HRrest correlation table TB1 can be stored in memory, and the age to resting heart rate HRrest correlation table TB1 can be referenced to set the resting heart rate HRrest based on the input age.

Although the present invention has been described in connection with the preferred embodiments thereof with reference to the accompanying drawings, it is to be noted that various changes and modifications will be apparent to those skilled in the art. Such changes and modifications are to be understood as included within the scope of the present invention as defined by the appended claims, unless they depart therefrom.

The entire disclosure of Japanese Patent Application Nos. 2006-333190 filed on Dec. 11, 2006, 2007-207466 filed on Aug. 9, 2007 and 2007-308573 filed on Nov. 29, 2007 are expressly incorporated by reference herein.

What is claimed is:

1. A biometric information processing device comprising:
   a heart rate detection unit that detects a heart rate of a subject;
   a relative heart rate calculation unit that calculates a relative heart rate, which is obtained from a first difference over a second difference, the first difference being by subtracting a prescribed resting heart rate of the subject from the heart rate, the second difference being by subtracting the prescribed resting heart rate from a maximum heart rate being based on an age of the subject;
   a relative oxygen intake calculation unit that calculates a relative oxygen intake based on the relative heart rate;
   an oxygen intake estimation unit that estimates the oxygen intake from the relative oxygen intake; and
   a calorie expenditure calculation unit that calculates calorie expenditure based on the oxygen intake,
   HR being the heart rate,
   HRrest being the resting heart rate,
   HRmax being a peak heart rate defined as a function of age of the subject,
   the relative heart rate calculation unit calculating the relative heart rate RHR using the HR, the HRrest and the Hrmax,
   when the relative heart rate is smaller than a predetermined value, the relative Oxygen Intake being regarded as 0.

2. The biometric information processing device described in claim 1, wherein:
   the resting heart rate is the value of the resting heart rate measured in a prescribed resting state before the start of exercise, or a value input externally by the user, or a value obtained by referencing a predefined table that stores correlations between age and the resting heart rate.

3. The biometric information processing device described in claim 2, wherein:
   the calorie expenditure calculation unit eliminates from the calorie expenditure calculation data about the oxygen intake acquired in a prescribed heart rate range in which the heart rate is considered to fluctuate easily due to psychological effects on the user when resting.

4. The biometric information processing device described in claim 1, further comprising:
   RHRmax being the relative heart rate;
   RVO$_2$max being the relative oxygen intake;
   an approximation unit that calculates an approximation function representing the relationship between the experimentally determined relative heart rate RHRmax and the relative oxygen intake RVO$_2$max and determines a slope and a intercept of the approximation function; and
   the relative oxygen intake calculation unit calculating relative oxygen intake RVO$_2$max using the elative heart rate RHRmax, the slope and the intercept.

5. The biometric information processing device described in claim 1, further comprising:
   VO$_2$max being a maximum oxygen intake;
   VO$_2$rest being a resting oxygen intake indicating the basal metabolism level; and
   a relative oxygen intake estimation unit calculating the oxygen intake VO$_2$ from the following equation:
   $$VO_2 = RVO_2\text{max}*(VO_2\text{max} - VO_2\text{rest}) + VO_2\text{rest}.$$

6. The biometric information processing device described in claim 5, wherein:
   the maximum oxygen intake VO$_2$max is an externally input user-defined value, or a value acquired from a predefined table that stores a correlation between the maximum oxygen intake VO$_2$max and one or more values selected from a group of values containing age, sex, and physical fitness, and including at least the age.

7. The biometric information processing device described in claim 1, further comprising:
   a calorie expenditure data storage unit that stores the calorie expenditure calculated by the calorie expenditure calculation unit as calorie expenditure data.

8. The biometric information processing device described in claim 7, further comprising:
   a communication unit that is connected to an external device over a communication network and sends the calorie data to the external device.

9. The biometric information processing device described in claim 1, further comprising:
   an activity level determination unit that determines the subject is exercising if the relative heart rate is greater than or equal to a prescribed reference relative heart rate;
   wherein the calorie expenditure calculation unit uses different operations to calculate calorie expenditure when the subject is exercising and when the subject is resting.

10. The biometric information processing device described in claim 9, wherein:
    the calorie expenditure calculation unit sets the calorie expenditure to zero when the subject is in the state of greatest rest.

11. The biometric information processing device according to claim 1, wherein
    the predetermined value is between 0% and 20%.

* * * * *